United States Patent [19]

Iwao et al.

[11] Patent Number: 4,482,709
[45] Date of Patent: Nov. 13, 1984

[54] INCLUSION COMPOUNDS OF CYCLODEXTRIN WITH SULFUR-CONTAINING COMPOUNDS

[75] Inventors: Jun-ichi Iwao, Takarazuka; Tadashi Iso, Sakai; Masayuki Oya, Ibaraki, all of Japan

[73] Assignee: Santen Pharmaceutical Co., Ltd., Osaka, Japan

[21] Appl. No.: 432,929

[22] PCT Filed: Feb. 24, 1982

[86] PCT No.: PCT/JP82/00050

§ 371 Date: Sep. 30, 1982

§ 102(e) Date: Sep. 30, 1982

[87] PCT Pub. No.: WO82/02890

PCT Pub. Date: Sep. 2, 1982

[30] Foreign Application Priority Data

Feb. 28, 1981 [JP] Japan ................... 56-29060

[51] Int. Cl.³ .................. C08B 37/16; A61K 31/73
[52] U.S. Cl. ...................... 536/46; 424/180; 424/361
[58] Field of Search .............. 536/46; 424/180, 361

[56] References Cited

U.S. PATENT DOCUMENTS

| | | | |
|---|---|---|---|
| 435,618 | 10/1982 | Iwao et al. | 424/263 |
| 3,246,025 | 4/1966 | Meta et al. | |
| 4,046,889 | 9/1977 | Ondetti et al. | 424/267 |
| 4,053,651 | 10/1977 | Ondetti et al. | 424/319 |
| 4,137,420 | 1/1979 | Fujita et al. | 562/426 |
| 4,241,086 | 12/1980 | Iwao et al. | 424/319 |
| 4,256,761 | 3/1981 | Suh et al. | 424/319 |
| 4,264,620 | 4/1981 | Iwao et al. | 424/274 |
| 4,305,958 | 12/1981 | Fujita et al. | 424/319 |
| 4,347,371 | 8/1982 | Iwao et al. | 548/201 |

FOREIGN PATENT DOCUMENTS

| | | |
|---|---|---|
| 50-94108 | 7/1975 | Japan . |
| 50-89516 | 7/1975 | Japan . |
| 50-116617 | 9/1975 | Japan . |
| 54-5916 | 1/1979 | Japan . |
| 57-26656 | 2/1982 | Japan . |
| 57-32260 | 2/1982 | Japan . |

OTHER PUBLICATIONS

The Merck Index, 1976, No. 5701.

The Extra Pharmacopoeia, 1977, 27th ed., p. 1822.
M. L. Bender, M. Komiyama, "Cyclodextrin no Kagaku", 4/15/79, pp. 49-57, translation p. 55.
Takamura, Shuichi et al., Chem. Abstracts, vol. 83, 1975, Item 152384e.
Kawamura, Shigeo et al., Chem. Abstracts, vol. 83, 1975, Item 197823p.
Nagai, Tsuneji, Chem. Abstracts, vol. 84, 1976, Item 84:111654v.
Fujita, Kimiji et al., Chem. Abstracts, vol. 91, 1979, Item 91:21117n.

*Primary Examiner*—Johnnie R. Brown
*Assistant Examiner*—Elli Peselev
*Attorney, Agent, or Firm*—Frishauf, Holtz, Goodman & Woodward

[57] ABSTRACT

This invention relates to inclusion compounds of cyclodextrin with the compounds of the general formula [I] and salts thereof, which show pharmacological effects (for example antihypertensive effect),

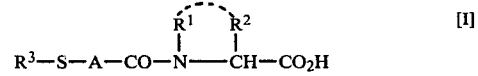

wherein
A is straight or branched lower alkylene;
$R^1$ is hydrogen or lower alkyl;
$R^2$ is hydrogen, lower alkyl, phenyl, phenyl-lower alkyl, hydroxyphenyl-lower alkyl, hydroxy-lower alkyl, amino-lower alkyl, guanidino-lower alkyl, imidazolyl-lower alkyl, indolyl-lower alkyl, mercapto-lower alkyl or lower alkylthio-lower alkyl;
$R^1$ or $R^2$ may join to complete pyrrolidine ring or thiazolidine ring, and each ring may be substituted by phenyl or pyridyl, and phenyl may be resubstituted by hydroxy, lower alkoxy, halogen, nitro or sulfamoyl;
$R^3$ is hydrogen or

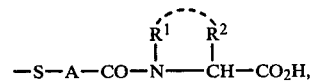

said lower alkyl and lower alkoxy having 1 to 6 carbon atoms.

12 Claims, No Drawings

INCLUSION COMPOUNDS OF CYCLODEXTRIN WITH SULFUR-CONTAINING COMPOUNDS

TECHNICAL FIELD OF THE INVENTION

This invention relates to inclusion compounds of cyclodextrin with the compounds of the general formula [I] and salts thereof,

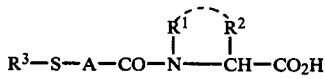

wherein
A is straight or branched lower alkylene;
$R^1$ is hydrogen or lower alkyl;
$R^2$ is hydrogen, lower alkyl, phenyl, phenyl-lower alkyl, hydroxyphenyl-lower alkyl, hydroxy-lower alkyl, amino-lower alkyl, guanidino-lower alkyl, imidazolyl-lower alkyl, indolyl-lower alkyl, mercapto-lower alkyl or lower alkylthio-lower alkyl;
$R^1$ and $R^2$ may join to complete pyrrolidine ring or thiazolidine ring, and each ring may be substituted by phenyl or pyridyl, and phenyl may be resubstituted by hydroxy, lower alkoxy, halogen, nitro or sulfamoyl;
$R^3$ is hydrogen or

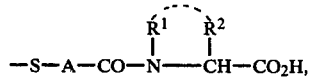

said lower alkyl and lower alkoxy having 1 to 6 carbon atoms.
The same shall be applied hereinafter.

BACKGROUND OF THE INVENTION

The compound of the formula [I] is a known compound, which shows antihypertensive effect, antirheumatic effect, suppresive effect of liver damage, liquefactive effect of sputum, etc. (Japanese Kokai Koho SHO 54-148783 corresponding to U.S. Pat. No. 4,356,183, Japanese Kokai Koho SHO 55-7255 corresponding to U.S. Pat. No. 4,356,183, U.S. Pat. No. 4,046,889, Japanese Kokai Koho SHO-55-51020 corresponding to U.S. Pat. No. 4,241,086, Japanese Pat. No. 1,066,721 corresponding to U.S. Pat. No. 4,305,958 and Japanese Pat. No. 432,636 corresponding to U.S. Pat. No. 3,246,025) U.S. Pat. Nos. 4,053,651, and 4,347,371.

But, disadvantages of the compound of the formula [I] exist in its less stability and/or low solubility in water, and these problems have not been solved.

DESCRIPTION OF THE INVENTION

This invention relates to inclusion compounds of cyclodextrin with the compounds of the general formula [I] and salts thereof.

The compound of the formula [I] is a known compound, which shows antihypertensive effect, antirheumatic effect, suppresive effect of liver damage, liquefactive effect of sputum, etc.

But, disadvantages of the compound of the formula [I] exist in its less stability and/or low solubility in water.

In order to improve the stability and solubility of the compound of the formula [I], the inventors made the compound of the formula [I] react with cyclodextrin to examine whether it forms the inclusion compound. As the result, the stable inclusion compound could be obtained by the reaction of the compound of the formula [I] with cyclodextrin, and the solubility of some of the resulting inclusion compounds in water became much higher than the original compound.

The method for preparing inclusion compound of this invention is for example as follows.

Cyclodextrin, preferably β-cyclodextrin, is dissolved in water or in a mixture of water and organic solvent which can be miscible with water, and compound [I] or a solution of compound [I] in water-miscible organic solvent is added, preferably by warming. The resulting solution is cooled, concentrated in vacuo or lyophilized to give a inclusion compound.

Water-miscible organic solvent is for example methanol, ethanol, n-propanol, isopropanol, acetone or dimethylformamide.

The ratio of water and organic solvent is chosen according to the solubility of the starting material and the resulting inclusion compound. Inclusion compound of this invention occurs as crystals or a powder and has a constant composition.

In IR spectrum of this inclusion compound, an absorption signal of carboxy group is 1700–1750 $cm^{-1}$.

Content of the compound [I] can be calculated by UV absorption spectrophotometry or iodometry. Consequentry, a stability and/or solubility in water of the inclusion compound became much higher than those of compound [I].

Solubility Test

Solubility in water of inclusion compound of cyclodextrin with compound A or compound C is shown below. As the result, the inclusion compound is extremely more soluble in water than the starting compound.

| Compound | Solubility in water |
| --- | --- |
| Compound of Example 1 | 1.0 g/100 ml |
| Compound of Example 3 | 0.07 g/100 ml |
| Compound A | 0.16 g/100 ml |
| Compound C | 0.01 g/100 ml |

Stability Test

Preservation test of the inclusion compound of Example 1 and compound A in water or phosphate buffer (pH 7.0) for one month at room temperature proved that the former compound is extremely more stable than the latter compound.

EXAMPLE 1

Inclusion compound of cyclodextrin with (2R,4R)-2-(2-hydroxyphenyl)-3-(3-mercaptopropanoyl)-4-thiazolidinecarboxylic acid (compound A)

0.6 g of compound A and 2.3 g of β-cyclodextrin are dissolved in 70 ml of hot water. The reaction mixture is filtered and concentrated in vacuo. Produced crystals are filtered to give 2.3 g of the titled compound.

mp > 250° C.

IR (nujol, $cm^{-1}$): 3340, 1730, 1655, 1335, 1290, 1240, 1205, 1155, 1080, 1030, 940, 860.

Content of the compound A in the crystals is 20%.

EXAMPLE 2

Inclusion compound of cyclodextrin with (2S)-1-[(2S)-3-mercapto-2-methylpropanoyl]-2-pyrrolidinecarboxylic acid (compound B)

0.4 g of compound B and 2.3 g of β-cyclodextrin are dissolved in 50 ml of hot water. The reaction mixture is filtered and concentrated in vacuo. A small amount of water is added to the residue and produced crystals are filtered to give 2.2 g of the titled compound.

mp > 250° C.

IR (nujol, $cm^{-1}$): 3340, 1730, 1640, 1330, 1240, 1200, 1155, 1080, 1025, 940, 870.

Content of the compound B in the crystals is 14%.

EXAMPLE 3

Inclusion compound of cyclodextrin with (4R,4'R)-3,3'-[3,3'-dithiobis(propanoyl)]bis[2-(2-hydroxyphenyl)-4-thiazolidinecarboxylic acid] (compound C)

To 85 ml of hot water solution of 6.3 g of β-cyclodextrin 10 ml of acetone solution of 0.4 g of compound C is added and the reaction mixture is filtered. The filtrate is stored for one night and produced crystals are filtered to give 1.6 g of the titled compound.

mp > 250° C.

IR (nujol, $cm^{-1}$): 3340, 1720, 1705, 1630, 1600, 1290, 1235, 1200, 1150, 1050, 940, 850.

Content of the compound C in the crystals is 14%.

EXAMPLE 4

Inclusion compound of cyclodextrin with N-(2-mercapto-2-methylpropanoyl)-L-cysteine (compound D)

1.1 g of compound D and 5.7 g of β-cyclodextrin are dissolved in 50 ml of hot water and the solution is stored for one night. Produced crystals are filtered to give 5.4 g of the titled compound.

mp 250°-251° C. (dec.)

IR (KBr, $cm^{-1}$): 3360, 1735, 1655, 1360, 1327, 1150, 1075, 1023, 937, 850.

Content of the compound D in the crystals in 14%.

EXAMPLE 5

Inclusion compound of cyclodextrin with N-(2-mercapto-propanoyl)glycine (compound E)

0.8 g of compound E and 5.7 g of β-cyclodextrin are dissolved in 60 ml of hot water. The solution is freeze-dried to give the titled compound.

UTILITY IN AN INDUSTRIAL FIELD

This invention offers novel compounds which are useful for therapeutic agents, the compounds have an anti-hypersensitive effect, anti-rheumatic effect, suppress the effect of liver damage, and are capable of liquifying sputum.

What we claim is:

1. An inclusion complex of cyclodextrin with a compound of formula [I] and pharmaceutically acceptable salts thereof,

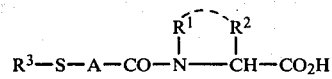

wherein

A is straight or branched lower alkylene;

$R^1$ is hydrogen or lower alkyl;

$R^2$ is selected from the group consisting of hydrogen, lower alkyl, phenyl, phenyl-lower alkyl, hydroxyphenyl-lower alkyl, hydroxy-lower alkyl, amino-lower alkyl, guanidino-lower alkyl, imidazolyl-lower alkyl, indolyl-lower alkyl, mercapto-lower alkyl and lower alkylthio-lower alkyl;

wherein $R^1$ and $R^2$ may join to complete a pyrrolidine ring or a thiazolidine ring, and each of said rings may be substituted by a substituent selected from the group consisting of phenyl, phenyl substituted with hydroxy, lower alkoxy, halogen, nitro and sulfamoyl, and pyridyl;

$R^3$ is hydrogen or

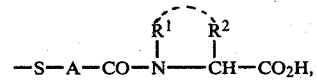

said lower alkyl and lower alkoxy having 1 to 6 carbon atoms.

2. The inclusion complex of claim 1, wherein $R^3$ is hydrogen.

3. The inclusion complex of claim 1, wherein $R^3$ is

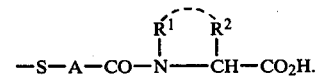

4. The inclusion complex of claim 1, wherein A is selected from the group consisting of —CH₂CH₂—, —CH₂CH(CH₃)—, —C(CH₃)₂— and —CH(CH₃)—.

5. The inclusion complex of claim 1, wherein the compound of formula [I] is (2R,4R)-2-(2-hydroxyphenyl)-3-(3mercaptopropanoyl)-4-thiazolidinecarboxylic acid.

6. The inclusion complex of claim 1, wherein the compound of formula [I] is (2S)-1-[(2S)-3-mercapto-2-methylpropanoyl]-2-pyrrolidinecarboxylic acid.

7. The inclusion complex of claim 1, wherein the compound of formula [I] is (4R,4'R)-3,3'-[3,3'-dithiobis(propanoyl)]bis-[2-(2-hydroxyphenyl)-4-thiazolidinecarboxylic acid].

8. The inclusion complex of claim 1, wherein the compound of formula [I] is N-(2-mercapto-2-methylpropanoyl)-L-cysteine.

9. The inclusion complex of claim 1, wherein the compound of formula [I] is N-(2-mercaptopropanoyl)glycine.

10. The inclusion complex of claim 2, wherein A is is selected from the group consisting of —CH₂CH₂—, —CH₂CH(CH₃)—, —C(CH₃)₂— and —CH(CH₃).

11. The inclusion complex of claim 2, wherein A is is selected from the group consisting of —CH₂CH₂—, —CH₂CH(CH₃)—, —C(CH₃)₂— and —CH(CH₃).

12. The inclusion complex of claim 1, wherein said cyclodextrin is beta-cyclodextrin.

* * * * *